United States Patent
Baxter

(10) Patent No.: US 6,610,030 B1
(45) Date of Patent: Aug. 26, 2003

(54) BILATERAL SYRINGE TETHERED REMOTE MICRO-PUMP

(76) Inventor: Anthony Baxter, 36 Cottage St., East Boston, MA (US) 02128

( * ) Notice: Subject to any disclaimer, the term of this patent is extended or adjusted under 35 U.S.C. 154(b) by 314 days.

(21) Appl. No.: 09/619,040

(22) Filed: Nov. 7, 2000

Related U.S. Application Data

(60) Provisional application No. 60/144,855, filed on Jul. 20, 1999.

(51) Int. Cl.[7] .......................... A61M 37/00; A61M 5/00
(52) U.S. Cl. ..................... 604/155; 604/154; 604/246
(58) Field of Search ............................ 604/131, 151, 604/154, 155, 246, 890.1; 222/251, 135, 293–296; 417/572

(56) References Cited

U.S. PATENT DOCUMENTS

| | | | | |
|---|---|---|---|---|
| 4,563,175 A | * | 1/1986 | LaFond | 604/155 |
| 4,846,797 A | * | 7/1989 | Howson et al. | 604/154 |
| 5,244,461 A | * | 9/1993 | Derlien | 604/65 |
| 5,423,752 A | * | 6/1995 | Haber et al. | 604/86 |
| 6,248,093 B1 | * | 6/2001 | Moberg | 604/131 |
| 6,475,188 B1 | * | 11/2002 | Baxter | 604/131 |

* cited by examiner

Primary Examiner—Brian L. Casler
Assistant Examiner—Catherine Serke

(57) ABSTRACT

A microinjection pump for administration of fluid pharmacological compounds to unrestrained and freely behaving animals is provided. The micro-pump employs a screw drive mechanism that is actuated by a small stepper motor. The pump moves fluids by direct mechanical displacement from two micro-syringes arranged in parallel. The drive mechanism incorporates a threaded central drive screw that is attached to the stepper motor drive shaft, The threads of the central drive screw engage the threads of two parallel, but oppositely turned (left hand turned and right hand turned) threaded rods. By the frictional action of the helical threads of the threaded drive screw with the threads of the threaded rods the threaded rods are moved linearly and depress the plungers of the attached micro-liter syringes. Medications are administered to animals through flexible tubing. An attached electrical swivel allows power to be delivered to the pump motor while allowing the micro-injector to pivot and move with the animal without binding or twisting the flexible tubing.

2 Claims, 1 Drawing Sheet

BILATERAL SYRINGE TETHERED REMOTE MICRO-PUMP

This application claims the benefit of Provisional application No. 60/144855, filed Jul. 20, 1999.

BACKGROUND OF THE INVENTION

1. Field of the Invention

This invention relates to the field of syringe pumps, in which syringes are placed with their plungers connected by syringe holders to the drive mechanisms of the pumps that push the plungers of the syringe barrels at a controlled rate to force the contents of the syringe out at a controlled rate into tubing that leads to a patient, research animal or analytical apparatus.

2. Description of the Related Art

Generally, syringe pumps are known in the medical arts as well as in biological, experimental psychological research and biotechnology industry. Their use includes the dispensing of medications or solutions to patients, research animals and for accurately dispensing for later mixing of fluid compounds for analysis (e.g. blood analysis) and in cellular (e.g. cloning) and tissue culture research where dispensing very small and accurate volumetric amounts is required.

Examples of prior art devices in the field are disclosed in the following U.S. Patents.

U.S. Pat. No. 4,563,175 discloses a syringe pump that houses three syringes and the associated separate drive mechanisms for the delivery of fluids from each of the syringes of various volumetric capacities. This pump is intended for use in patients and for administering several fluids at different rates. Fluid volumes delivered are in the milliliter range. The pump, though intended for human use, contains no fluid or electrical swivel to prevent binding and blockage of flexible tubing. The central drive screw employed in this machine is not a true worm gear, but rather a central drive screw that frictionally engages the helical threads of a central drive member and, thereby, moves an attached arm that depresses a plunger on a housed syringe. This is distinctly unlike my invention that employs two micro-syringes, has an electrical swivel, employs two oppositely turned threaded rods that convert the rotary motion of a central drive screw to linear motion by frictional engagement with the threads of the drive screw and push the plungers of the bilaterally arranged micro-syringes.

U.S. Pat. No. 6,248,093 B1 discloses a cylindrical piston pump that incorporates a rotating drive screw (split lead screw design) and internally threaded cylinder. In this design, an attached motor turns the drive screw, which engages the threads of an internal segment that advances a middle and outer segment that together to expel fluid from the cylinder. The screw drive mechanism works in one cylinder only. The amount of fluid moved is not in the micro-liter or nano-liter range but in the range required for human pharmaceutical delivery which is generally in the cubic centimeter or milliliter range. No fluid or electrical swivel is employed. Drive mechanism is significantly different from the three member threaded rod mechanism of my invention in which two separate threaded rods are moved linearly by the frictional engagement of their threads with the threads of the rotating central drive screw. The device disclosed in U.S. Pat. No. 6,248,093 is not intended or can it be applied to research animal use wherein animal subjects can move freely while self-administering micro-liter or nano-liter volume amounts; its use is limited to human drug administration. My invention can be used in both human and animal applications and can be incorporated in analytical apparatus as a result of its very small size, unlike the device in U.S. Pat. No. 6,248,093. That machine also requires an O ring for water sealing, whereas the pump of my invention does not.

U.S. Pat. No. 6,475,188 discloses a bilateral micro injector pump for freely moving animals in an operant chamber. The pump employs a stepper motor and a central screw drive mechanism. A recirculating micro-ball bearing slide and guide are employed as a frictionless carrier for the plunger depressing block. Block and ball-bearing slide comprise a "knee" that converts the rotary motion of the stepper motor into linear motion and depresses the plungers of two micro-syringes arranged in parallel. The pump uses an electrical swivel to deliver electricity to the drive mechanism. The pump extrudes from nano-liter to micro-liter volumes from both micro-syringes simultaneously. The pump also contains an electrical swivel that allows the pump to move as the animal freely behaves so that the flexible tubes do not become bent or bound up and, thereby, restrict the flow of fluid. In response to the assertion that the ball-bearing slide and guide may allow microscopic lateral "play" in the linear drive mechanism, and that the "knee" itself may bind with the threaded hole in the knee and, thereby cause intermittent interruption in the smooth continuous and accurate movement of the syringe plungers and consequent problematic and inaccurate extrusion of fluid from the syringes, I developed my present invention. My invention overcomes this asserted problem by a completely different mechanism that is illustrated in FIG. 1 of this application. A three member drive apparatus whose threaded rod components move without friction with the pump housing; there is friction only where the central drive screw meets the two threaded rods (where rotary motion is converted to linear motion). The invention also eliminates the size, weight, lateral "play", and drive screw/knee binding problem of the machine is U.S. Pat. No. 6,475,188 while, at the same time, delivering unit nano-liter volumes from both micro-syringes simultaneously and incorporating an electrical swivel for movement of the pump without constriction and consequent obstruction of fluid flow through the flexible tubing that delivers fluids to freely behaving subjects.

U.S. Pat. No. 4,846,797 discloses a syringe positioning device that holds four syringes in parallel. It employs classical rack and pinion gears that are connected to and depress the plungers of the syringes. That design is quite different from the three threaded rod component design of the drive mechanism in my invention illustrated in FIG. 1. The positioning system of U.S. Pat. No. 4,846,797 is not a true pump but only the positioning system. Its motor drive was not disclosed. It is not intended for animal use and is not capable of delivering micro-liter or nano-liter volumes. It does not contain a fluid or electrical swivel. It is also much larger than my invention.

U.S. Pat. No. 5,423,752 discloses a hand held variable proportion dispenser that is actuated manually by the patient administering the medication. Two separate medications can be dispensed together from the same outlet needle. The drive mechanism utilizes a screw positioning mechanism that allows the patient to set the amount to be self-administered. The dispenser is not intended for any use other than human manual medication administration. The screw set mechanism is significantly different from the drive mechanism employed in my invention illustrated in FIG. 1.

SUMMARY OF THE INVENTION

A micro-pump for administration of fluid compounds to freely behaving animals is provided. The drive mechanism of the pump contains a screw drive mechanism that overcomes the limitations of prior art devices discussed in the Background of the Invention section of this application. In the preferred embodiment, the micro-pump provides enhanced control over the accurate dispensing of from nano-liter to micro-liter volumes of fluid compounds to freely moving animals. It is therefore an object of this invention to provide a device for the delivery of accurate and identical volumes of fluids from two syringes simultaneously.

DESCRIPTION OF THE PREFERRED EMBODIMENT

Figure 1:
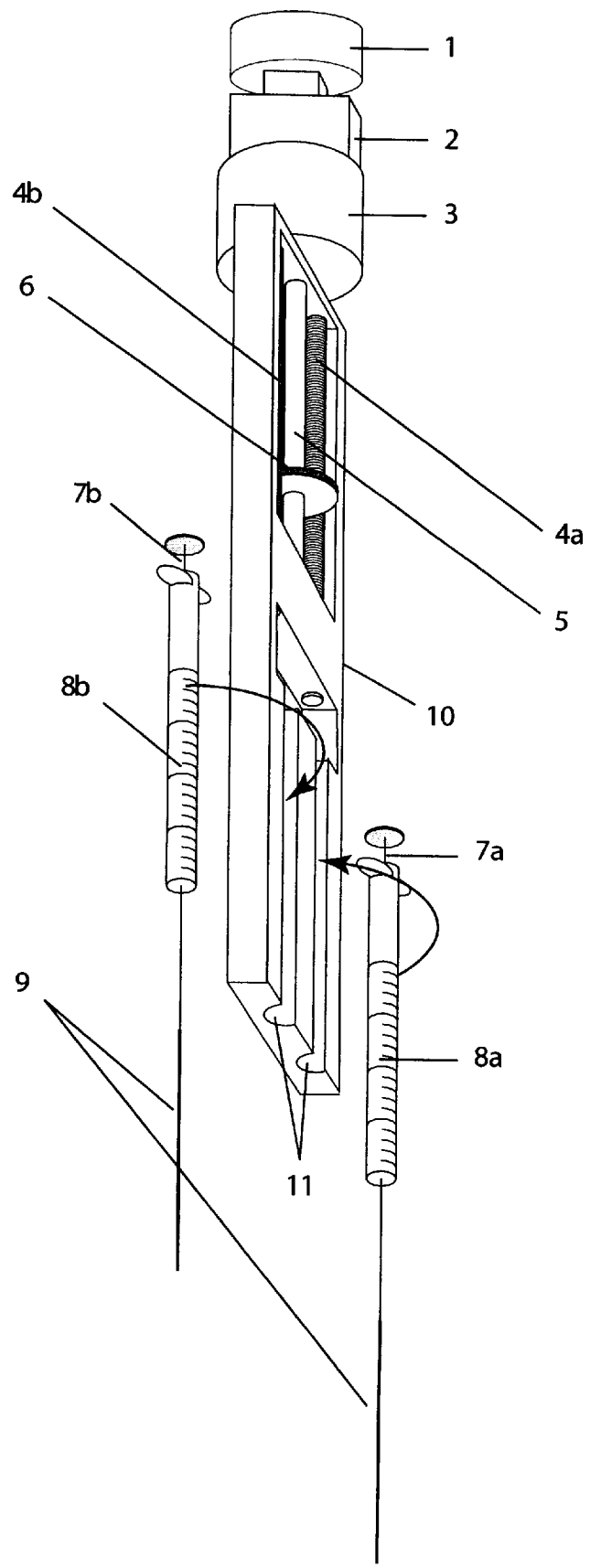
FIG. 1 is as perspective view of the micro-injector including the drive mechanism, motor, electrical swivel, commutator, syringes and syringe holder.

FIG. 1 is a perspective view of the micro-injection pump in accordance with this invention with an electrical swivel 1 is attached to a 4 channel commutator 2 which is secured to a stepper motor 3 that is mounted to a pump housing 10. A drive shaft 5 is bolted to a central drive screw 6 whose threads engage both a left hand turned threaded rod 4a and a right hand turned threaded rod 4b so that the friction produced by the rotating central drive screw with the threaded rods moves both threaded rods linearly in the same direction. Both threaded rods depress the plungers 7a, 7b of two micro-syringes 8a, 8b that are held stationary and in parallel within the syringe clamp 11. Fluids are extruded through flexible tubing 9.

This design converts the rotary motion of the stepper motor that turns the drive shaft into linear motion of the threaded rods. Linear distance of the threaded rods is determined by the steps of the motor and the pitch of the threaded rods and the drive screw. Associated electronics give the motor step size of 15 degrees (24 steps per 360 degree revolution).

The modular design and construction of the pump allows the easy interchange and replacement of the threaded rods with alternate threaded rods and, thereby, allows variation of the relative amounts of fluids that can be delivered by the injector micro-syringe.

The pump can accomplish all of this while tethered to a freely moving animal because the electrical connections are made through an electrical swivel that is attached to both the stepper motor and the body of the pump allowing the pump to pivot and turn freely. The electrical swivel obviates the need for a fluid swivel which are inconsistent and unreliable in their delivery of the very small fluid amounts needed for neuroscience research.

Although the specific embodiment has been described with reference to a micro-injection pump for freely moving animals, the micro-injection pump of the invention may be used wherever accurate nano-liter and micro-liter and milliliter volumes are to be delivered over predetermined periods, for example in medical, research and analytical and industrial purposes.

What is claimed is:

1. A tethered remote bilateral micro-injection pump for infusing fluid pharmacological compounds comprising: a central drive screw having threads, two threaded rods having threads of the same pitch as the central drive screw, one of the threaded rods having left hand turned threads and the other of the threaded rods having right hand turned threads, the threaded rods are removable and interchangeable with alternate threaded rods of the same diameter having different thread pitch thereby allowing variability in a rate of linear movement and fluid extrusion from two bilaterally arranged micro-syringes comprising two barrels with each of the two barrels having a plunger head and a micro-syringe clamp holding the two barrels stationary, wherein the threads of the two threaded rods engage the threads of the central screw in a manner similar to both a rack and pinion and a worm drive allowing both threaded rods to move in a same direction when engaged by the central drive screw that is rotating in a clockwise direction whereby the threaded rods depress each of the plunger heads of the two bilaterally arranged micro-syringes causing extrusion of fluid from the micro-syringes into and through capillary tubing attached to the micro-syringes for delivery of fluids into a freely behaving animal.

2. The micro-injection pump according to claim 1, further comprising a stepper motor affixed to the central drive screw by a bolt, a 4 channel electrical swivel communicator and modular socket connector wired to the stepper motor, associated electronics providing a motor step size of 15 degrees, wherein the bolt and the central drive screw are turned in a rotary and stepwise manner by the stepper motor and thereby through friction move the two threaded rods in the same direction, wherein in a reverse driving mode, the stepper motor and the central drive screw cause the two threaded rods to move in an opposite direction, retracting the plungers, taking up fluid and filling the micro-syringes.

* * * * *